United States Patent
Konno et al.

(10) Patent No.: US 10,538,543 B2
(45) Date of Patent: Jan. 21, 2020

(54) METHOD FOR PRODUCING CYCLOMETALATED IRIDIUM COMPLEX, AND CYCLOMETALATED IRIDIUM COMPLEX PRECURSOR INCLUDING ORGANOIRIDIUM MATERIAL

(71) Applicants: NATIONAL INSTITUTE OF ADVANCED INDUSTRIAL SCIENCE AND TECHNOLOGY, Tokyo (JP); TANAKA KIKINZOKU KOGYO K.K., Tokyo (JP)

(72) Inventors: Hideo Konno, Tsukuba (JP); Junichi Taniuchi, Tsukuba (JP); Rumi Kobayashi, Tsukuba (JP); Yasushi Masahiro, Tokyo (JP)

(73) Assignees: NATIONAL INSTITUTE OF ADVANCED INDUSTRIAL SCIENCE AND TECHNOLOGY, Tokyo (JP); TANAKA KIKINZOKU KOGYO K.K., Tokyo (JP)

( * ) Notice: Subject to any disclaimer, the term of this patent is extended or adjusted under 35 U.S.C. 154(b) by 0 days.

(21) Appl. No.: 16/331,978

(22) PCT Filed: Oct. 12, 2017

(86) PCT No.: PCT/JP2017/036935
§ 371 (c)(1),
(2) Date: Mar. 10, 2019

(87) PCT Pub. No.: WO2018/079275
PCT Pub. Date: May 3, 2018

(65) Prior Publication Data
US 2019/0256539 A1    Aug. 22, 2019

(30) Foreign Application Priority Data
Oct. 24, 2016    (JP) .................................. 2016-207483

(51) Int. Cl.
*C07F 15/00* (2006.01)
(52) U.S. Cl.
CPC ................................ *C07F 15/0033* (2013.01)
(58) Field of Classification Search
CPC .................................................. C07F 15/0033
See application file for complete search history.

(56) References Cited

U.S. PATENT DOCUMENTS

| | | |
|---|---|---|
| 2004/0169463 A1 | 9/2004 | Burn et al. |
| 2005/0116622 A1 | 6/2005 | Lo et al. |
| 2006/0142604 A1 | 6/2006 | Bach et al. |
| 2008/0211391 A1 | 9/2008 | Burn et al. |
| 2010/0127251 A1 | 5/2010 | Burn et al. |
| 2011/0272688 A1 | 11/2011 | Burn et al. |
| 2016/0326198 A1 | 11/2016 | Konno et al. |
| 2017/0166599 A1 | 6/2017 | Abe et al. |

FOREIGN PATENT DOCUMENTS

| | | |
|---|---|---|
| CN | 103601760 A | 2/2014 |
| CN | 104447545 A | 3/2015 |
| JP | 2003-231692 A | 8/2003 |
| WO | WO-02/067343 A1 | 8/2002 |
| WO | WO-03/079736 A2 | 9/2003 |
| WO | WO-2004/085449 A1 | 10/2004 |
| WO | WO-2006/097717 A1 | 9/2006 |
| WO | WO-2015/104961 A1 | 7/2015 |
| WO | WO-2016/006523 A1 | 1/2016 |

OTHER PUBLICATIONS

International Searching Authority, "International Search Report," issued in connection with International Patent Application No. PCT/JP2017/036935, dated Dec. 19, 2017.

International Searching Authority, "Written Opinion," issued in connection with International Patent Application No. PCT/JP2017/036935, dated Dec. 19, 2017.

Periana et al., "Novel bis-acac-O,Or(III) catalyst for anti-Markovnikov, hydroarylation of olefins operates by arene CH activation," Chem Comm, 2002, pp. 3000-3001.

Chang et al., "Study on the Coordinate Mode of Acetylacetonate in Ir(acac)$_3$ and Ir(acac)$_3$ (H$_2$O)," Precious Metals, vol. 32, No. 3, Aug. 2011, pp. 64-68.

Chang et al. "Bis(acetylacetonato-µ$^2$O,O')aqua-(diacetylmethanido-µC)iridium(III)," Acta Crystallographica, Section E65, m1264, pp. Sup-1-Sup-8. 2009.

(Continued)

*Primary Examiner* — Brenda L Coleman
(74) *Attorney, Agent, or Firm* — Foley & Lardner LLP

(57) ABSTRACT

The present invention provides a method for producing a cyclometalated iridium complex, the method including producing a cyclometalated iridium complex by reacting a cyclometalated iridium complex raw material including an organoiridium material with an aromatic heterocyclic bidentate ligand capable of forming an iridium-carbon bond and an iridium-nitrogen bond, and using as the raw material an organoiridium material represented by the following general formula (1). The present invention allows a cyclometalated iridium complex to be produced with a high yield without by-production of a halogen-crosslinked iridium dimer.

[Chemical Formula 1]

General Formula (1)

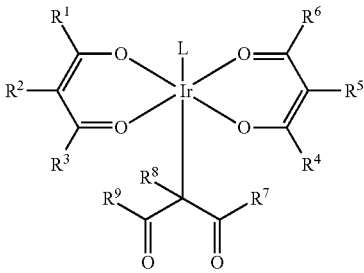

6 Claims, No Drawings

(56) References Cited

OTHER PUBLICATIONS

Teets et al., "Iridium Complexes, 39. The Diphosphine tfepma and its Diiridium Complex $Ir_2^{0,11}(tfepma)_3Cl_2$," Inorganic Syntheses, vol. 35, 2010, pp. 164-178.
Bhalla et al., "Alkane C-H Bond Activation by O-Donor Ir Complexes," American Chemical Society, 2004, pp. 105-115.
Bhalla et al., "Synthesis, Structure, and Reactivity of O-Donor Ir(III) Complexes: C-H Activation Studies with Benzene," Journal of American Chemical Society, vol. 127, 2005, pp. 11372-11389.

METHOD FOR PRODUCING CYCLOMETALATED IRIDIUM COMPLEX, AND CYCLOMETALATED IRIDIUM COMPLEX PRECURSOR INCLUDING ORGANOIRIDIUM MATERIAL

RELATED APPLICATIONS

The present application claims priority under 37 U.S.C. § 371 to International Patent Application No. PCT/JP2017/036935, filed Oct. 12, 2017, which claims priority to and the benefit of Japanese Patent Application No. 2016-207483, filed on Oct. 24, 2016. The contents of these applications are hereby incorporated by reference in their entireties.

TECHNICAL FIELD

The present invention relates to a technique for producing a cyclometalated iridium complex with a high yield and a high purity. The cyclometalated iridium complex is used as a phosphorescent material for organic electroluminescent (EL) devices, organic electrochemiluminescent (ECL) devices, luminescent sensors, photosensitizing pigments, photocatalysts, luminescent probes, various light sources, and the like.

BACKGROUND ART

Organic EL devices obtained by use of a phosphorescent material have light-emitting efficiency three to four times higher than that of conventional organic EL devices obtained by use of a fluorescent material, and thus are being extensively researched and developed. As a phosphorescent material, an iridium complex is known in which an aromatic heterocyclic bidentate ligand such as 2-phenylpyridine or 1-phenylisoquinoline is cyclometalated by forming an iridium-carbon bond and an iridium-nitrogen bond (see Chemical Formula 1).

[Chemical Formula 1]

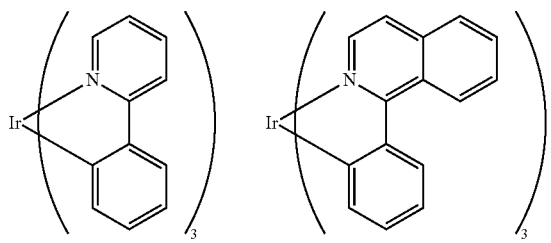

Regarding a method for producing the cyclometalated iridium complex, Patent Document 1 discloses a method in which bis(acetylacetonato)dichloroiridium (III) acid sodium (Chemical Formula 2) as an iridium compound that is a raw material is reacted with an aromatic heterocyclic bidentate ligand such as 2-phenylpyridine or 1-phenylisoquinoline.

[Chemical Formula 2]

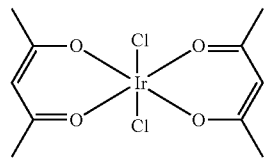

RELATED ART DOCUMENT

Patent Document

Patent Document 1: WO 2004/085449 A1

SUMMARY OF THE INVENTION

Problems to be Solved by the Invention

However, according to findings of the present inventor, use of an aromatic heterocyclic bidentate ligand in a large amount is required for producing a cyclometalated iridium complex represented by Chemical Formula (1). Specifically, it was revealed that a desired cyclometalated iridium complex was not produced with practical efficiency unless an excessive amount of aromatic heterocyclic bidentate ligand was used in a molar amount as much as 10 times or more the molar amount of iridium raw material. Many aromatic heterocyclic bidentate ligands are expensive, and this method considerably increases the cost of the cyclometalated iridium complex.

In addition, regarding the problem of the use amount of aromatic heterocyclic bidentate ligand, at least a desired cyclometalated iridium complex can be produced even though a considerably excessive amount of ligand concerned is not used in the method described in Patent Document 1. In this case, however, by-products such as a halogen-crosslinked iridium dimer are produced, and a desired cyclometalated iridium complex alone cannot be obtained. The problem was revealed that rather the yield of by-products was higher, and a desired cyclometalated iridium complex could not be obtained with a favorable yield and purity.

Further, additional studies by the present inventor revealed that there was an instance where side reactions such as decomposition of reactants proceeded in the method described in Patent Document 1. In such an instance, the yield of a desired cyclometalated iridium complex is not improved even if the use amount of aromatic heterocyclic bidentate ligand is increased.

The present invention has been made in view of the above-mentioned situations, and discloses a new method by which a cyclometalated iridium complex that is suitably used as a phosphorescent material for an organic EL device can be produced with a high yield and a high purity without by-production of a halogen-crosslinked iridium dimer.

Means for Solving the Problems

For solving the above-described problems, the present invention provides a method for producing a cyclometalated iridium complex, the method including producing a cyclometalated iridium complex by reacting a cyclometalated iridium complex raw material including an organoiridium material with an aromatic heterocyclic bidentate ligand capable of forming an iridium-carbon bond and an iridium-nitrogen bond, and using as the raw material an organoiridium material represented by the following general formula (1).

[Chemical Formula 3]

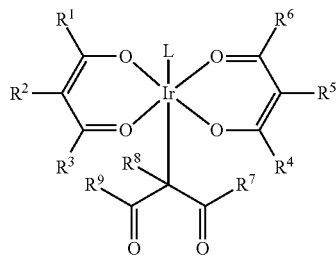

General Formula (1)

(In General Formula (1), Ir represents an iridium atom, and O represents an oxygen atom; L represents a ligand capable of forming an iridium-oxygen bond; $R^1$, $R^3$, $R^4$, $R^6$, $R^7$ and $R^9$ each represent an alkyl group; $R^2$, $R^5$ and $R^8$ each represent a hydrogen atom or an alkyl group; and some or all of hydrogen atoms of the alkyl group may be substituted with halogen atoms).

The present inventors have extensively conducted studies on a method for producing a cyclometalated iridium complex, and resultantly found a method for producing a cyclometalated iridium complex, characterized by using an organoiridium material having a specific structure represented by General Formula (1) as an iridium raw material.

With the method for producing a cyclometalated iridium complex of the present invention, a desired cyclometalated iridium complex can be produced with a favorable yield. The reason for this has not necessarily been evident, but the present inventors consider as follows.

The present invention allows a cyclometalated iridium complex to be produced with a favorable yield principally because a halogen-crosslinked iridium dimer is generated. That is, bis(acetylacetonato)dichloroiridium (III) acid sodium which is an iridium raw material in the conventional art has a halogen ligand. Thus, there is the problem that a halogen-crosslinked iridium dimer which is an undesired by-product is easily generated. On the other hand, the organoiridium material of General Formula (1) which is used as a raw material in the present invention does not contain any halogen ligand. Therefore, in the production method of the present invention, a halogen-crosslinked iridium dimer is not generated at all.

In addition, the iridium compound of General Formula (1) which is applied as an iridium raw material in the present invention has a relatively weak bond between the ligand L and iridium (iridium-oxygen bond), and this may also be a factor of improvement of the yield. That is, in the present invention, the ligand L of the iridium raw material can be more easily desorbed than the halogen ligand of the iridium raw material in the conventional art (bis(acetylacetonato) dichloroiridium (III) acid sodium). Thus, the yield of the cyclometalated iridium complex desired may be dramatically improved.

The present inventors have found that in the method for producing a cyclometalated iridium complex of the present invention, side reactions such as decomposition of reactants hardly proceed. This is also a factor of improvement of the yield of the cyclometalated iridium complex.

Further, in the method for producing a cyclometalated iridium complex of the present invention, it is required to react an iridium compound with an aromatic heterocyclic bidentate ligand, but in the present invention in which the iridium compound of General Formula (1) is used as a raw material, a cyclometalated iridium complex can be produced without use of an excessive amount of the aromatic heterocyclic bidentate ligand. Thus, the use amount of expensive aromatic heterocyclic bidentate ligand is reduced, so that a cyclometalated iridium complex can be produced at low cost.

Hereinafter, the method for producing a cyclometalated iridium complex of the present invention will be described in detail. Hereinafter, (I) iridium raw material, (II) aromatic heterocyclic bidentate ligand and (III) suitable reaction conditions which constitute the present invention will be described.

(I) Iridium Raw Material

As described above, the iridium raw material to be applied in the present invention is an iridium compound represented by General Formula (1). In General Formula (1), Ir represents an iridium atom, and O represents an oxygen atom.

L represents a ligand capable of forming an iridium-oxygen bond (hereinafter, sometimes referred to as an Ir-oxygen bond) for iridium. The ligand capable of forming an Ir-oxygen bond is preferably a neutral ligand. Examples of the ligand include $H_2O$ ligands, alcohol ligands (preferably having a carbon number of 1 to 10, more preferably 1 to 6, especially preferably 1 to 3), acetic acid ligands, trifluoroacetic acid ligands, and trifluoromethanesulfonic acid ligands. The ligand is preferably a $H_2O$ ligand or an alcohol ligand, more preferably a $H_2O$ ligand or a methanol ligand, especially preferably a $H_2O$ ligand.

$R^1$, $R^3$, $R^4$, $R^6$, $R^7$ and $R^9$ in General Formula (1) each independently represent an alkyl group. Some or all of hydrogen atoms of the alkyl group may be substituted with halogen atoms (preferably fluorine atoms). The desired range of the carbon number in the alkyl group is the same as that in the alkyl group which can be linked to CyA and CyB as described later.

$R^1$, $R^3$, $R^4$, $R^6$, $R^7$ and $R^9$ are each preferably a methyl group, an ethyl group, a n-propyl group, an isopropyl group, a n-butyl group, an isobutyl group, a sec-butyl group, a tert-butyl group or a trifluoromethyl group, more preferably a methyl group, an isopropyl group or a trifluoromethyl group, especially preferably a methyl group.

$R^2$, $R^5$ and $R^8$ are each independently preferably a hydrogen atom or an alkyl group, more preferably a hydrogen atom or a methyl group, especially preferably a hydrogen atom.

Examples of the iridium compound represented by General Formula (1) are shown in Chemical Formula 4. Note that the raw material compound in the present invention is not limited to these iridium compounds. Among them, compounds (Ir-1) and (Ir-5) to (Ir-8) are preferable, compounds (Ir-1) and (Ir-5) to (Ir-7) are more preferable, and compound (Ir-1) is especially preferable.

[Chemical Formula 4]

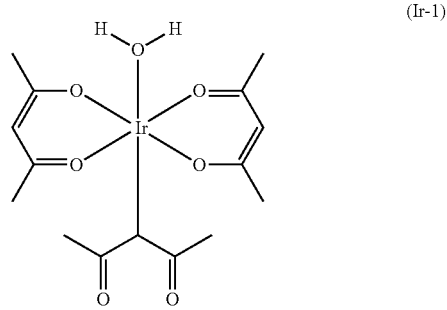

(Ir-1)

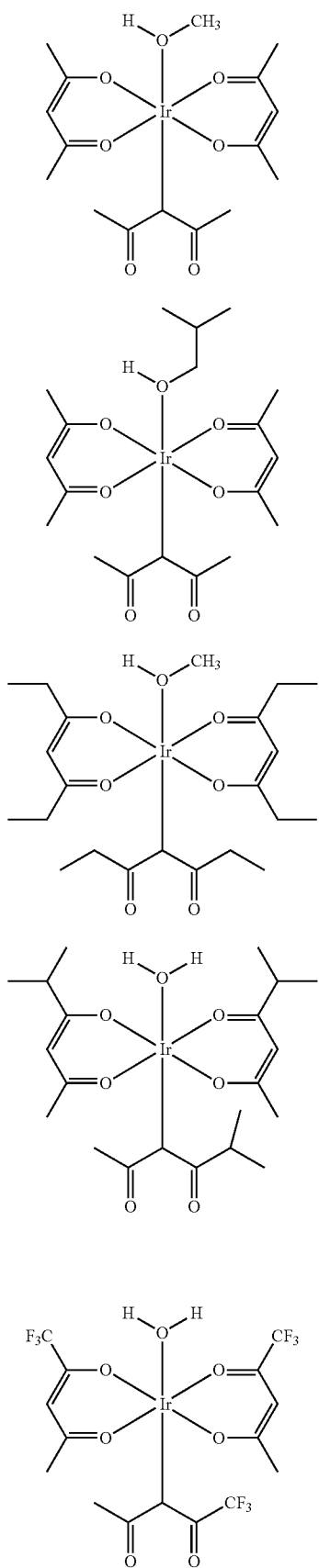

(Ir-2)

(Ir-3)

(Ir-4)

(Ir-5)

(Ir-6)

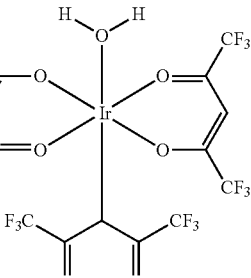

(Ir-7)

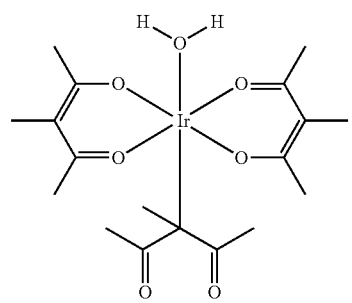

(Ir-8)

(II) Aromatic Heterocyclic Bidentate Ligand

The method for producing a cyclometalated iridium complex of the present invention includes reacting an aromatic heterocyclic bidentate ligand with the above-described iridium compound (general formula (1)).

The aromatic heterocyclic bidentate ligand in the production method of the present invention is preferably one represented by General Formula (2).

[Chemical Formula 5]

General Formula (2)

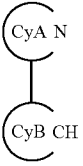

In General Formula (2), N represents a nitrogen atom, C represents a carbon atom, and H represents a hydrogen atom.

CyA represents a five-membered or six-membered cyclic group containing nitrogen atoms, and is linked to iridium via the nitrogen atoms. CyA is preferably a five-membered or six-membered nitrogen-containing aromatic heterocyclic ring.

CyB represents a five-membered or six-membered cyclic group containing carbon atoms, and is linked to iridium via the carbon atoms. CyB is preferably a five-membered or six-membered aromatic carbon ring or aromatic heterocyclic ring, more preferably a five-membered or six-membered aromatic carbon ring or nitrogen-containing aromatic heterocyclic ring, especially preferably a five-membered or six-membered aromatic carbon ring.

CyA and CyB may be linked together to form a new ring structure. Here, CyA and CyB are preferably linked together to form a new saturated ring or unsaturated ring, more preferably an unsaturated ring.

Examples of the five-membered or six-membered cyclic group containing nitrogen atoms include a pyridine ring, a pyrimidine ring, a pyrazine ring, a pyridazine ring, a quinoline ring, an isoquinoline ring, a quinoxaline ring, a cinnoline ring, a phthalazine ring, a quinazoline ring, a naphthyridine ring, an imidazole ring, a pyrazole ring, a triazole ring, a tetrazole ring, an oxazole ring, an oxadiazole ring, a thiazole ring, and a thiadiazole ring. Among them, a pyridine ring, a pyrimidine ring, a quinoline ring, an isoquinoline ring, an imidazole ring, a pyrazole ring, and a triazole ring are preferable, a pyridine ring, a quinoline ring, an isoquinoline ring, and an imidazole ring are more preferable, and a pyridine ring, an isoquinoline ring, and an imidazole ring are especially preferable.

Specific examples of the five-membered or six-membered cyclic group containing carbon atoms include a benzene ring, a naphthalene ring, an anthracene ring, a carbazole ring, a fluorene ring, a furan ring, a thiophene ring, a pyridine ring, a pyrimidine ring, a pyrazine ring, a pyridazine ring, a quinoline ring, an isoquinoline ring, a quinoxaline ring, a cinnoline ring, a phthalazine ring, a quinazoline ring, a naphthyridine ring, an imidazole ring, a pyrazole ring, a triazole ring, a tetrazole ring, an oxazole ring, an oxadiazole ring, a thiazole ring, and a thiadiazole ring. Among them, a benzene ring, a naphthalene ring, a pyridine ring, and a pyrimidine ring are preferable, a benzene ring, a pyridine ring, and a pyrimidine ring are more preferable, and a benzene ring is especially preferable.

Regarding a ring formed by linkage of CyA and CyB, CyA and CyB are linked together to preferably form a benzoquinoxaline ring, a benzoquinoline ring, a dibenzoquinoxaline ring, a dibenzoquinoline ring, or a phenanthridine ring, more preferably a benzoquinoline ring, a dibenzoquinoxaline ring, or a phenanthridine ring. The benzoquinoline ring is preferably a benzo[h]quinoline ring. The dibenzoquinoxaline ring is preferably a dibenzo[f,h]quinoxaline ring. The phenanthridine ring is preferably an imidazo[1,2-f]phenanthridine ring.

CyA, CyB and the ring formed by linkage of CyA and CyB may have substituents, may have adjacent substituents linked together to form a ring structure, and may be further substituted.

Examples of CyA, CyB, and the substituent which is linked to a ring formed by linkage of CyA and CyB include the following groups.

Alkyl groups (with a carbon number of preferably 1 or more and 30 or less, more preferably 1 or more and 20 or less, especially preferably 1 or more and 10 or less, e.g., methyl, ethyl, iso-propyl, tert-butyl, n-octyl, n-decyl, n-hexadecyl, cyclopropyl, cyclopentyl, and cyclohexyl).

Alkenyl groups (with a carbon number of preferably 2 or more and 30 or less, more preferably 2 or more and 20 or less, especially preferably 2 or more and 10 or less, e.g., vinyl, allyl, 2-butenyl, and 3-pentenyl).

Alkynyl groups (with a carbon number of preferably 2 or more and 30 or less, more preferably 2 or more and 20 or less, especially preferably 2 or more and 10 or less, e.g., propargyl and 3-pentynyl).

Aryl groups (with a carbon number of preferably 6 or more and 30 or less, more preferably 6 or more and 20 or less, especially preferably 6 or more and 12 or less, e.g., phenyl, p-methylphenyl, naphthyl, and anthranil).

Amino groups (with a carbon number of preferably 0 or more and 30 or less, more preferably 0 or more and 20 or less, especially preferably 0 or more and 10 or less, e.g., amino, methylamino, dimethylamino, diethylamino, dibenzylamino, diphenylamino, and ditolylamino).

Alkoxy groups (with a carbon number of preferably 1 or more and 30 or less, more preferably 1 or more and 20 or less, especially preferably 1 or more and 10 or less, e.g., methoxy, ethoxy, butoxy, and 2-ethylhexyloxy).

Aryloxy groups (with a carbon number of preferably 6 or more and 30 or less, more preferably 6 or more and 20 or less, especially preferably 6 or more and 12 or less, e.g., phenyloxy, 1-naphthyloxy, and 2-naphthyloxy).

Heterocyclic oxy groups (with a carbon number of preferably 1 or more and 30 or less, more preferably 1 or more and 20 or less, especially preferably 1 or more and 12 or less, e.g., pyridyloxy, pyrazyloxy, pyrimidyloxy, and quinolyloxy).

Acyl groups (with a carbon number of preferably 1 or more and 30 or less, more preferably 1 or more and 20 or less, especially preferably 1 or more and 12 or less, e.g., acetyl, benzoyl, formyl, and pivaloyl).

Alkoxycarbonyl groups (with a carbon number of preferably 2 or more and 30 or less, more preferably 2 or more and 20 or less, especially preferably 2 or more and 12 or less, e.g., methoxycarbonyl and ethoxycarbonyl).

Aryloxycarbonyl groups (with a carbon number of preferably 7 or more and 30 or less, more preferably 7 or more and 20 or less, especially preferably 7 or more and 12 or less, e.g., phenyloxycarbonyl).

Acyloxy groups (with a carbon number of preferably 2 or more and 30 or less, more preferably 2 or more and 20 or less, especially preferably 2 or more and 10 or less, e.g., acetoxy and benzoyloxy).

Acylamino groups (with a carbon number of preferably 2 or more and 30 or less, more preferably 2 or more and 20 or less, especially preferably 2 or more and 10 or less, e.g., acetylamino and benzoylamino).

Alkoxycarbonylamino groups (with a carbon number of preferably 2 or more and 30 or less, more preferably 2 or more and 20 or less, especially preferably 2 or more and 12 or less, e.g., methoxycarbonylamino).

Aryloxycarbonylamino groups (with a carbon number of preferably 7 or more and 30 or less, more preferably 7 or more and 20 or less, especially preferably 7 or more and 12 or less, e.g., phenyloxycarbonylamino).

Sulfonylamino groups (with a carbon number of preferably 1 or more and 30 or less, more preferably 1 or more and 20 or less, especially preferably 1 or more and 12 or less, e.g., methanesulfonylamino and benzenesulfonylamino).

Sulfamoyl groups (with a carbon number of preferably 0 or more and 30 or less, more preferably 0 or more and 20 or less, especially preferably 0 or more and 12 or less, e.g., sulfamoyl, methylsulfamoyl, dimethylsulfamoyl, and phenylsulfamoyl).

Carbamoyl groups (with a carbon number of preferably 1 or more and 30 or less, more preferably 1 or more and 20 or less, especially preferably 1 or more and 12 or less, e.g., carbamoyl, methylcarbamoyl, diethylcarbamoyl, and phenylcarbamoyl).

Alkylthio groups (with a carbon number of preferably 1 or more and 30 or less, more preferably 1 or more and 20 or less, especially preferably 1 or more and 12 or less, e.g., methylthio and ethylthio).

Arylthio groups (with a carbon number of preferably 6 or more and 30 or less, more preferably 6 or more and 20 or less, especially preferably 6 or more and 12 or less, e.g., phenylthio).

Heterocyclic thio groups (with a carbon number of preferably 1 or more and 30 or less, more preferably 1 or more and 20 or less, especially preferably 1 or more and 12 or less, e.g., pyridylthio, 2-benzimizolylthio, 2-benzoxazolylthio, and 2-benzthiazolylthio).

Sulfonyl groups (with a carbon number of preferably 1 or more and 30 or less, more preferably 1 or more and 20 or less, especially preferably 1 or more and 12 or less, e.g., mesyl and tosyl).

Sulfinyl groups (with a carbon number of preferably 1 or more and 30 or less, more preferably 1 or more and 20 or less, especially preferably 1 or more and 12 or less, e.g., methanesulfinyl and benzenesulfinyl).

Ureide groups (with a carbon number of preferably 1 or more and 30 or less, more preferably 1 or more and 20 or less, especially preferably 1 or more and 12 or less, e.g., ureide, methylureide, and phenylureide).

Phosphoramide groups (with a carbon number of preferably 1 or more and 30 or less, more preferably 1 or more and 20 or less, especially preferably 1 or more and 12 or less, e.g., diethylphosphoramide and phenylphosphoramide).

Hydroxy groups, mercapto groups, halogen atoms (e.g., fluorine atom, chlorine atom, bromine atom, and iodine atom), cyano groups, sulfo groups, carboxyl groups, nitro groups, trifluoromethyl groups, hydroxamic acid groups, sulfino groups, hydrazino groups, imino groups, and heterocyclic groups (with a carbon number of preferably 1 or more and 30 or less, more preferably 1 or more and 12 or less and with a nitrogen atom, an oxygen atom, or a sulfur atom as a heteroatom, specifically, imidazolyl, pyridyl, quinolyl, furyl, thienyl, piperidyl, morpholino, benzoxazolyl, benzimidazolyl, benzothiazolyl, carbazolyl group, azepinyl group, and the like).

Silyl groups (with a carbon number of preferably 3 or more and 40 or less, more preferably 3 or more and 30 or less, especially preferably 3 or more and 24 or less, e.g., trimethylsilyl and triphenylsilyl).

Silyloxy groups (with a carbon number of preferably 3 or more and 40 or less, more preferably 3 or more and 30 or less, especially preferably 3 or more and 24 or less, e.g., trimethylsilyloxy and triphenylsilyloxy).

Among the above-mentioned substituents, alkyl groups, aryl groups, amino groups, alkoxy groups, aryloxy groups, halogen atoms, cyano groups, trifluoromethyl groups, heterocyclic groups, and silyl groups are preferable, alkyl groups, aryl groups, halogen atoms, cyano groups, and heterocyclic groups are more preferable, and alkyl groups and aryl groups are especially preferable. Among these substituents, those that are desirable are as described above, and these substituents may be further substituted with the above-mentioned substituents. Adjacent substituents may be linked together to form a ring structure.

As a desired form of the aryl group or heterocyclic group, a dendron (a group having a regular dendritic branched structure with a branch point at an atom or ring) is also preferable. Examples of the dendron include structures described in documents such as WO 02/067343 A1, JP 2003-231692 A, WO 2003/079736 A1, WO 2006/097717 A1, and WO 2016/006523 A1.

Examples of the specific preferred structure of the aromatic heterocyclic bidentate ligand represented by General Formula (2) for use in the present invention include structures shown in Chemical Formula 6 and represented by General Formulae (4) to (15). Among them, aromatic heterocyclic bidentate ligands having the structures represented by General Formulae (4) to (7) and (13) are preferable, and aromatic heterocyclic bidentate ligands having the structures represented by General Formulae (4), (6), (7) and (13) are more preferable.

[Chemical Formula 6]

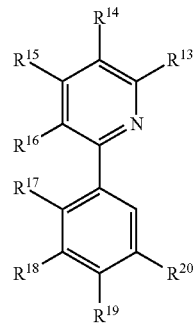

(4)

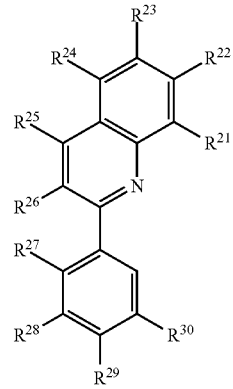

(5)

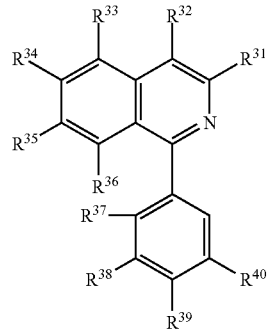

(6)

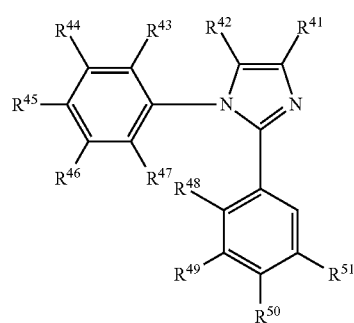

(7)

(8) 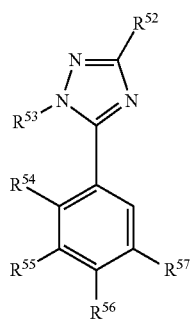

(9) 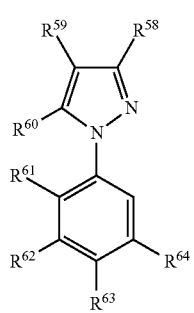

(10) 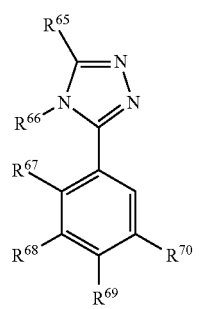

(11) 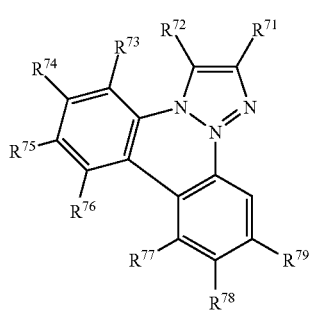

(12) 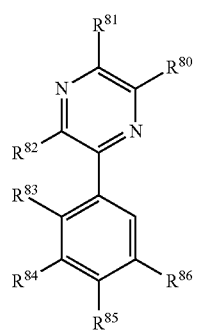

(13) 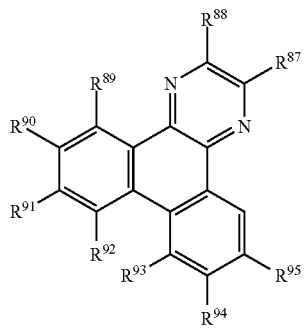

(14) 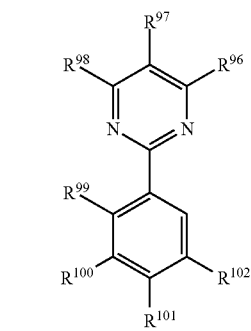

(15) 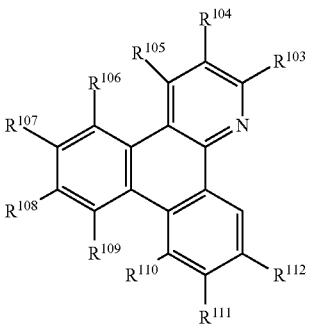

(In Formulae (4) to (15), $R^{13}$ to $R^{112}$ each independently represent a hydrogen atom or a substituent; adjacent substituents may be linked together to further form a ring structure; and the substituents $R^{13}$ to $R^{112}$ have the same meanings as those of the substituents described in CyA and CyB, and the same applies to a desired range).

In the present invention, the iridium compound represented by General Formula (1) is reacted with the aromatic heterocyclic bidentate ligand to produce a cyclometalated iridium complex. A preferred structure as the cyclometalated iridium complex is represented by General Formula (3).

[Chemical Formula 7]

General Formula (3)

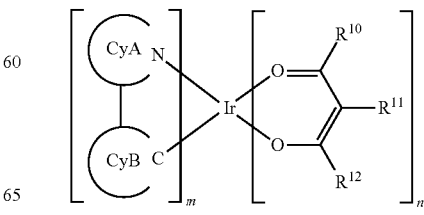

(In General Formula (3), Ir represents an iridium atom, N represents a nitrogen atom, C represents a carbon atom, CyA represents a five-membered or six-membered cyclic group containing nitrogen atoms, and is linked to iridium via the nitrogen atoms, and CyB represents a five-membered or six-membered cyclic group containing carbon atoms, and is linked to iridium via the carbon atoms; CyA and CyB may be linked together to further form a ring structure; $R^{10}$ and $R^{12}$ each independently represent an alkyl group, $R^{11}$s each independently represent a hydrogen atom or an alkyl group, and some or all of hydrogen atoms of the alkyl group may be substituted with halogen atoms; and m is 2 or 3, n is 0 or 1, and m+n is 3).

The definitions of N, C, CyA and CyB in General Formula (3) have the same meanings as in General Formula (2), and the same applies to the details of N, C, CyA and CyB, and the range of substituents to which N, C, CyA and CyB can be bonded.

(III) Suitable Reaction Conditions

Preferred reaction conditions in the method for producing a cyclometalated iridium complex of the present invention will be described.

Preferably, a solvent is used in the method for producing a cyclometalated iridium complex of the present invention. As the solvent, for example, an alcohol, a saturated aliphatic hydrocarbon, an ester, an ether, a nitrile, an aprotic polar solvent, a ketone, an amide, an aromatic hydrocarbon, a nitrogen-containing aromatic compound, an ionic liquid or water is preferable. Among them, the solvent is more preferably an alcohol, a saturated aliphatic hydrocarbon, an ester, an ether, an aprotic polar solvent, or an amide, especially preferably an alcohol or an aprotic polar solvent (DMF, DMSO, or the like), even more preferably an alcohol (with a carbon number of preferably 1 or more and 30 or less, more preferably 1 or more and 20 or less, still more preferably 1 or more and 10 or less). Among alcohol, diol (with a carbon number of preferably 1 or more and 30 or less, more preferably 1 or more and 20 or less, still more preferably 1 or more and 10 or less) is most preferable. Specifically, ethylene glycol, diethylene glycol, triethylene glycol, 1,2-propanediol, 1,3-propanediol, and 1,3-butanediol are preferable.

The above-mentioned solvents may be used singly, or two or more of the solvents may be used in combination.

In the method for producing a cyclometalated iridium complex of the present invention, the concentration of the iridium compound represented by General Formula (1) in the reaction system is not particularly limited, but is preferably 0.001 mol/L or more and 10.0 mol/L or less, more preferably 0.001 mol/L or more and 1.0 mol/L or less, still more preferably 0.01 mol/L or more and 1.0 mol/L or less, especially preferably 0.05 mol/L or more and 0.5 mol/L or less.

The use amount of the aromatic heterocyclic bidentate ligand in the method for producing a cyclometalated iridium complex of the present invention is preferably in the following range.

In the case of producing a cyclometalated iridium complex in which m is 3 and n is 0 in General Formula (3), the amount of the aromatic heterocyclic bidentate ligand is preferably 3 times or more and less than 10 times, more preferably 3 times or more and less than 6 times, especially preferably 3 times or more and less than 4.5 times the molar amount of the iridium compound represented by General Formula (1).

In the case of producing a cyclometalated iridium complex in which m is 2 and n is 1 in General Formula (3), the amount of the aromatic heterocyclic bidentate ligand is preferably 1.5 times or more and less than 3 times, more preferably 1.5 times or more and less than 2.5 times, especially preferably 2 times or more and less than 2.5 times the molar amount of the iridium compound represented by General Formula (1).

As described above, in the present invention, it is not necessary to use an excessive amount of the aromatic heterocyclic bidentate ligand for producing a cyclometalated iridium complex. Thus, the use amount of expensive aromatic heterocyclic bidentate ligand is reduced, so that the cost of the cyclometalated iridium complex can be reduced.

In the method for producing a cyclometalated iridium complex of the present invention, it is preferable that the reaction system including the iridium compound and the aromatic heterocyclic bidentate ligand is heated. The reaction temperature here is 50° C. or higher and lower than 300° C. The reaction temperature is preferably 50° C. or higher and lower than 250° C., more preferably 100° C. or higher and lower than 250° C., still more preferably 140° C. or higher and lower than 220° C., especially preferably 140° C. or higher and lower than 200° C. The heating means here is not particularly limited. Specifically, external heating using an oil bath, a sand bath, a mantle heater, a block heater, or a heat-circulation jacket, as well as heating by irradiation with microwaves can be utilized, for example.

In the method for producing a cyclometalated iridium complex of the present invention, the reaction time is not particularly limited. Note that the reaction time is preferably 0.5 hours or more and less than 72 hours, more preferably 1 hour or more and less than 48 hours, still more preferably 1 hour or more and less than 24 hours.

In the method for producing a cyclometalated iridium complex of the present invention, it is preferable that the reaction is carried out under an inert gas (e.g., nitrogen or argon) atmosphere. In addition, it is preferable that the reaction is carried out at normal pressure (under atmospheric pressure).

The cyclometalated iridium complex produced by the method of the present invention is treated by a general post-treatment method and then, after purification as necessary or without purification, can be used as a high-purity product. As the method for post-treatment, for example, extraction, cooling, crystallization by addition of water or an organic solvent, distillation of the solvent from the reaction mixture, and like operations may be performed alone or in combination. As the method for purification, recrystallization, distillation, sublimation, column chromatography, and the like may be performed alone or in combination.

The cyclometalated iridium complex produced by the above-described method of the present invention can be suitably used as a phosphorescent material for organic EL devices etc.

Advantageous Effects of the Invention

The present invention allows a cyclometalated iridium complex suitably used as a phosphorescent material for organic EL devices etc. to be produced with a high yield and a high purity. Since the iridium compound of General Formula (1) in the present invention has no halogen ligand, a halogen-crosslinked iridium dimer which is an undesired by-product is not produced in principle, and the production efficiency of a desired cyclometalated iridium complex can be considerably improved.

The iridium compound of General Formula (1) of the present invention is useful as a raw material for production of a cyclometalated iridium complex. By use of the iridium compound of General Formula (1), a desired cyclometalated iridium complex can be efficiently produced with a favorable purity.

DESCRIPTION OF EMBODIMENTS

Hereinafter, an embodiment of the present invention will be described in detail. In this embodiment, the iridium compound represented by General Formula (1) was reacted with the aromatic heterocyclic bidentate ligand to produce a cyclometalated iridium complex. This embodiment is one example of the present invention, and the present invention is not limited to this embodiment.

In this embodiment, the following iridium compound (Ir-1) was used as an iridium compound raw material to produce various cyclometalated iridium complexes (T-1, T-2, T-3, T-4, B-2 and B-4) in Table 1 (Examples 1 to 5). In addition, as comparative examples, an attempt was made to produce the same cyclometalated iridium complexes (T-1, T-2 and T-3) as in Examples 1 to 3 by use of bis(acetylacetonato)dichloroiridium (III) acid sodium (comparative compound-A) (Comparative Examples 1 to 3). The iridium compound (Ir-1) and the iridium compound (comparative compound-A) were produced in the following manner.

[Chemical Formula 8]
Iridium compund raw material

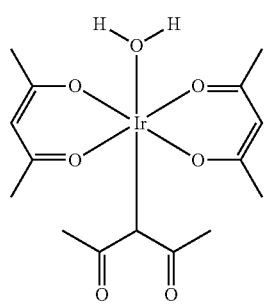
(Ir-1)

Comparative compound-A

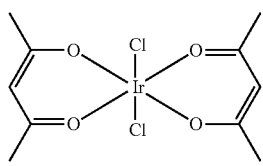

Cyclometalated iridium complex

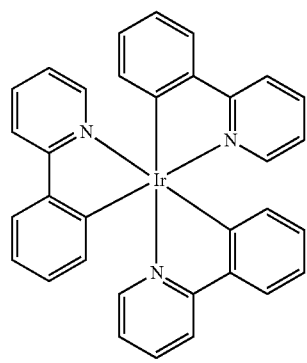
(T-1)

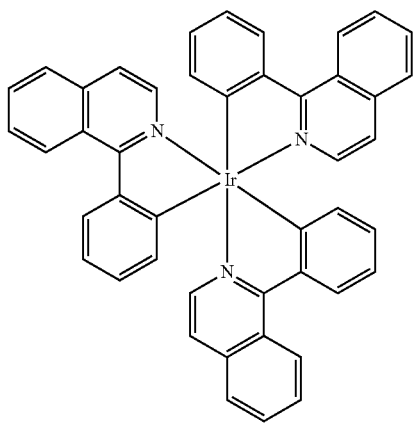
(T-2)

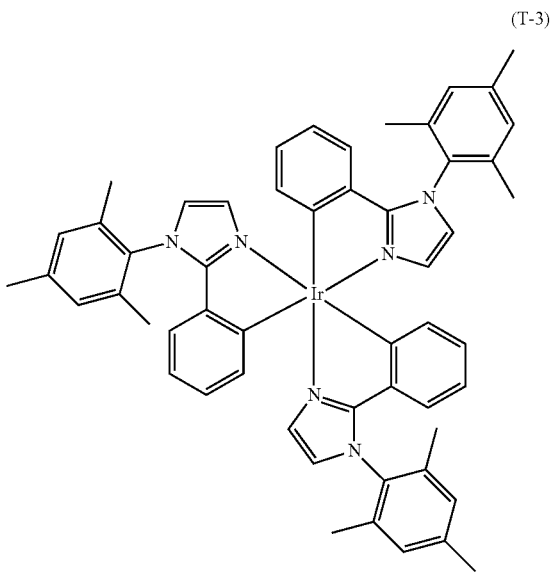
(T-3)

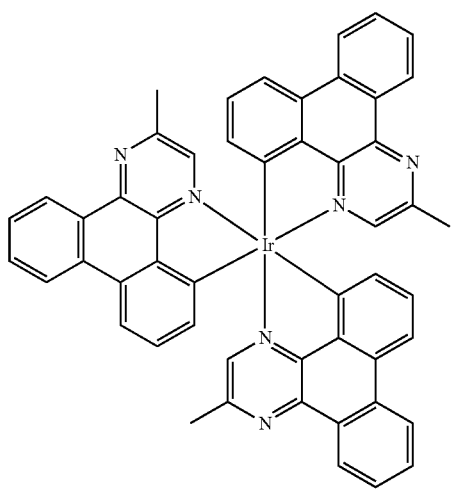
(T-4)

-continued (B-2)

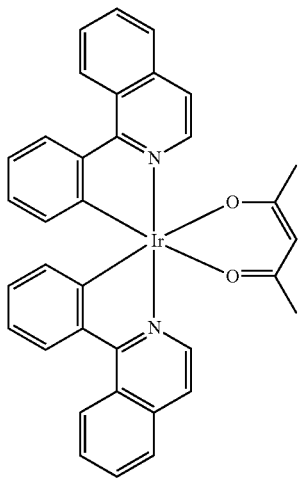

(B-4)

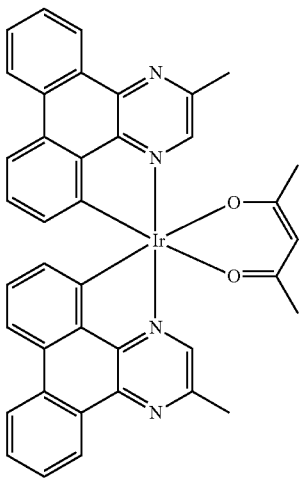

[Method for Producing Iridium Compound (Ir-1)]

85.1 g (234.1 mmol) of iridium trichloride trihydrate was added to 850.5 ml (8.3 mol) of acetylacetone, 84.9 g (1.0 mol) of sodium hydrogen carbonate was further added, and the mixture was reacted in an argon atmosphere at 110° C. for 48 hours. After the reaction, the reaction product was allowed to cool overnight, precipitated by addition of 1 L of dichloromethane, filtered, and dried under vacuum to obtain a yellow crude crystal. For washing the crude crystal, 400 ml of dichloromethane was added, the mixture was filtered, and dried under vacuum twice. The crude crystal was recrystallized with pure water to obtain 16.4 g of a yellow crystal of the iridium compound (Ir-1).

[Method for Producing Iridium Compound (Comparative Compound-A)]

37.1 g (105 mmol) of iridium trichloride trihydrate was dissolved in 200 ml of pure water, 200 ml of 1 M sodium hydrogen carbonate and 20.5 ml (200 mmol) of acetylacetone were added, and the mixture was reacted at 95° C. for 10 hours. After the reaction, the reaction product was dried by vacuum drying, 400 ml of methanol was added, and the mixture was refluxed for 8 hours, and then filtered. The filtrate was concentrated, and cold methanol was added to obtain 13.0 g of a crystal of the iridium compound (comparative compound-A).

<Example 1>: Synthesis of Cyclometalated Iridium Complex (T-1)

104.2 mg (0.2 mmol) of the iridium compound (Ir-1), 108.6 mg (0.7 mmol) of 2-phenylpyridine and 1.7 ml of ethylene glycol were mixed, and the mixture was heated and reacted in an argon atmosphere at 180° C. for 17 hours. After completion of the reaction, the reaction solution was cooled to room temperature, and a yellow solid precipitated by addition of methanol to the reaction solution was recovered.

The result of analysis of $^1$H-NMR showed that the product was a desired cyclometalated iridium complex (T-1), and the yield was 62%. The reaction formula here is shown below.

[Chemical Formula 9]

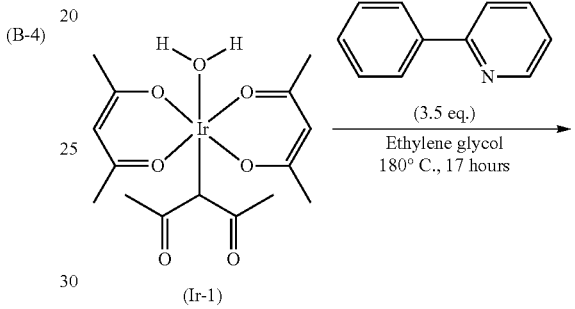

(Ir-1)

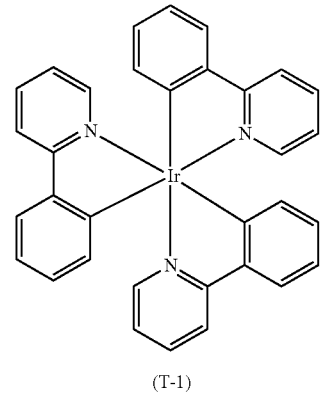

(T-1)

<Comparative Example 1>: Synthesis of Cyclometalated Iridium Complex (T-1) (Comparative Compound-A)

145.3 mg (0.3 mmol) of the comparative compound-A, 163.0 mg (1.05 mmol) of a 2-phenylpyridine ligand and 2.5 ml of ethylene glycol were mixed, and the mixture was heated and reacted in an argon atmosphere at 180° C. for 17 hours. After completion of the reaction, the reaction solution was cooled to room temperature, and a yellow solid precipitated by addition of methanol to the reaction solution was recovered.

The result of analysis of $^1$H-NMR showed that the product was a mixture of a desired cyclometalated iridium complex (T-1) and a halogen-crosslinked iridium dimer (D-1). The yield of (T-1) and (D-1) were 22% and 73%, respectively. The reaction formula here is shown below.

[Chemical Formula 10]

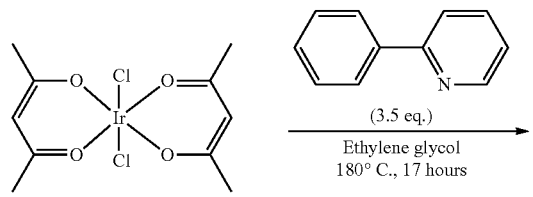

Comparative compound-A

Ethylene glycol
180° C., 17 hours
(3.5 eq.)

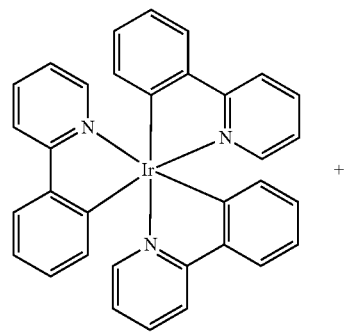

(T-1)

+

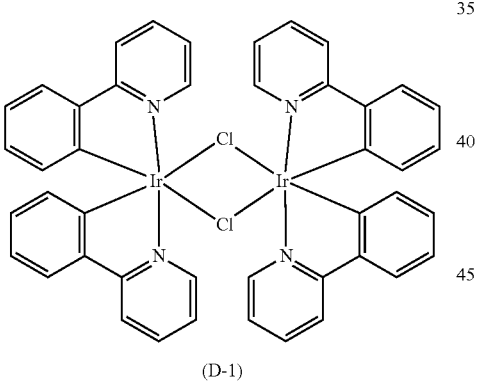

(D-1)

[Chemical Formula 11]

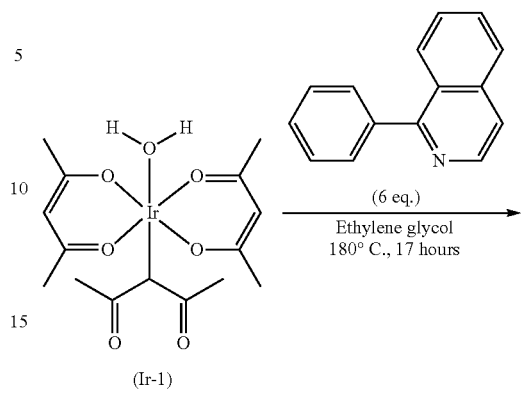

(Ir-1)

Ethylene glycol
180° C., 17 hours
(6 eq.)

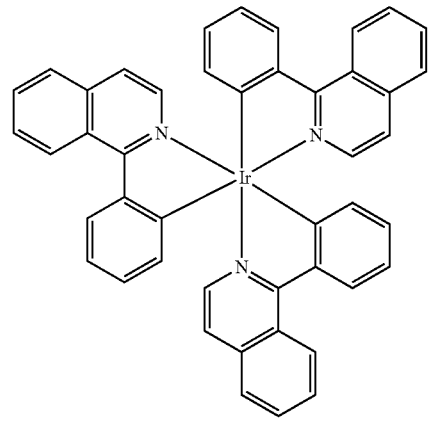

(T-2)

<Example 2>: Synthesis of Cyclometalated Iridium Complex (T-2)

104.2 mg (0.2 mmol) of the iridium compound (Ir-1), 246.3 mg (1.2 mmol) of 1-phenylisoquinoline and 1.7 ml of ethylene glycol were mixed, and the mixture was heated and reacted in an argon atmosphere at 180° C. for 17 hours. After completion of the reaction, the reaction solution was cooled to room temperature, and a red solid precipitated by addition of methanol to the reaction solution was recovered.

The result of analysis of $^1$H-NMR showed that the product was a desired cyclometalated iridium complex (T-2), and the yield was 60%. The reaction formula here is shown below.

<Comparative Example 2>: Synthesis of Cyclometalated Iridium Complex (T-2) (Comparative Compound-A)

145.3 mg (0.3 mmol) of the comparative compound-A, 369.5 mg (1.8 mmol) of 1-phenylisoquinoline and 2.5 ml of ethylene glycol were mixed, and the mixture was heated and reacted in an argon atmosphere at 180° C. for 17 hours. After completion of the reaction, the reaction solution was cooled to room temperature, and a red solid precipitated by addition of methanol to the reaction solution was recovered.

The result of analysis of $^1$H-NMR showed that the product was a mixture of a desired cyclometalated iridium complex (T-2) and a halogen-crosslinked iridium dimer (D-2). The yields of (T-2) and (D-2) were 24% and 66%, respectively. The reaction formula here is shown below.

[Chemical Formula 12]

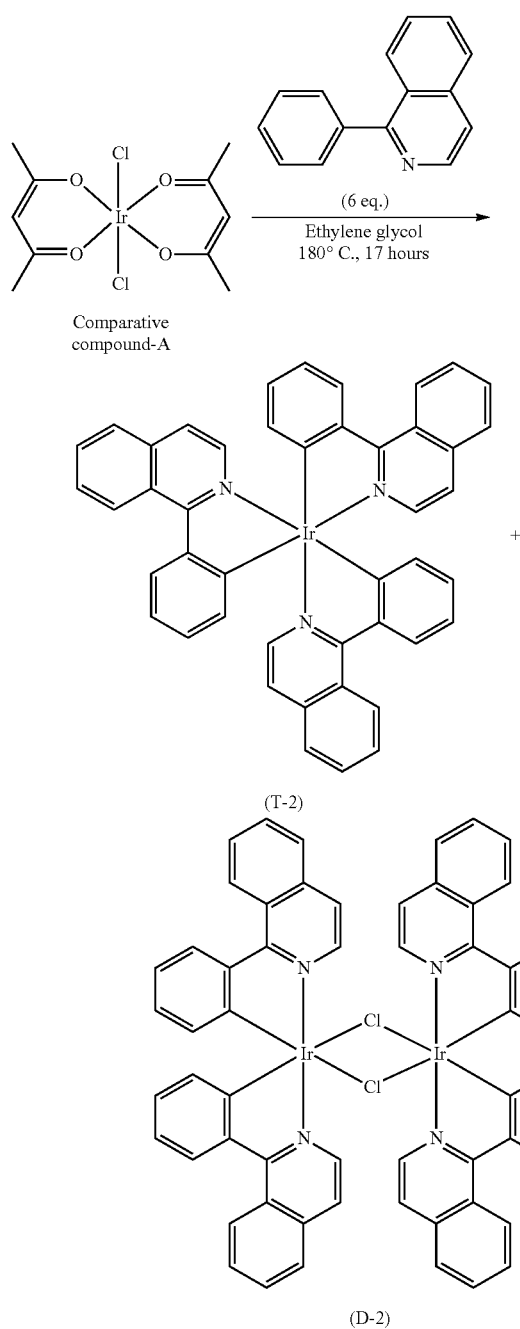

<Example 3>: Synthesis of Cyclometalated Iridium Complex (T-3)

208.4 mg (0.4 mmol) of the iridium compound (Ir-1), 367.3 mg (1.4 mmol) of 1-mesityl-2-phenyl-1H-imidazole and 0.5 ml of ethylene glycol were mixed, and the mixture was heated and reacted in an argon atmosphere at 180° C. for 17 hours. After completion of the reaction, the reaction solution was cooled to room temperature, and a yellow solid precipitated by addition of methanol to the reaction solution was recovered.

The result of analysis of $^1$H-NMR showed that the product was a desired cyclometalated iridium complex (T-3), and the yield was 54%. The reaction formula here is shown below.

[Chemical Formula 13]

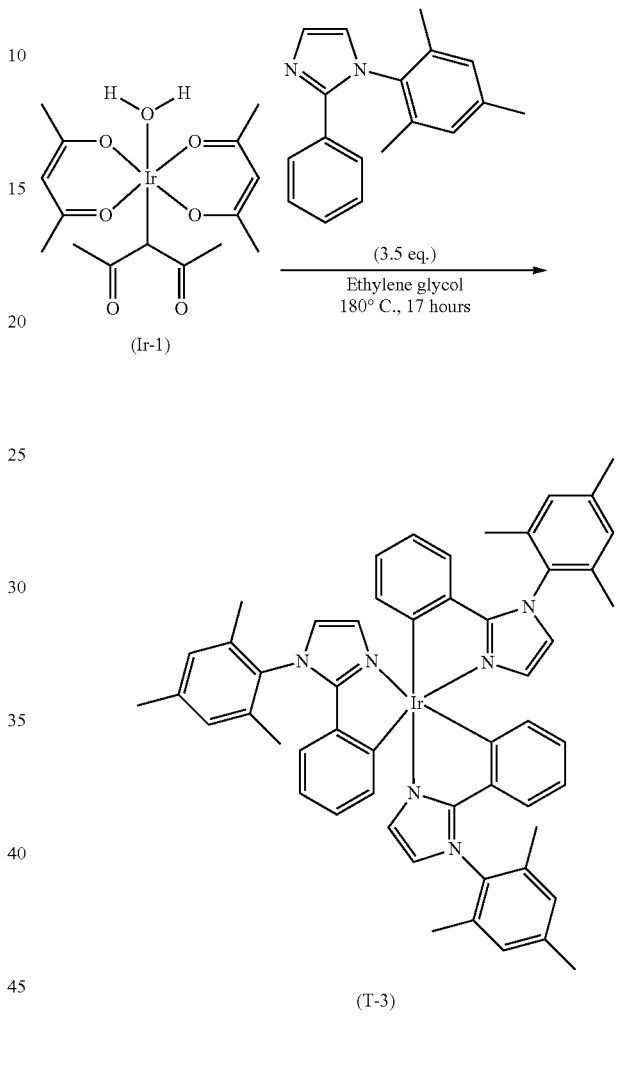

<Comparative Example 3>: Synthesis of Cyclometalated Iridium Complex (T-3) (Comparative Compound-A)

145.3 mg (0.3 mmol) of the comparative compound-A, 275.5 mg (1.05 mmol) of 1-mesityl-2-phenyl-1H-imidazole and 2.5 ml of ethylene glycol were mixed, and the mixture was heated and reacted in an argon atmosphere at 180° C. for 17 hours. After completion of the reaction, the reaction solution was cooled to room temperature, and a yellow solid precipitated by addition of methanol to the reaction solution was recovered.

The result of analysis of $^1$H-NMR showed that the product was a halogen-crosslinked iridium dimer (D-3) alone, and the yield was 23%. A desired cyclometalated iridium complex (T-3) was not obtained at all. The reaction formula here is shown below.

[Chemical Formula 14]

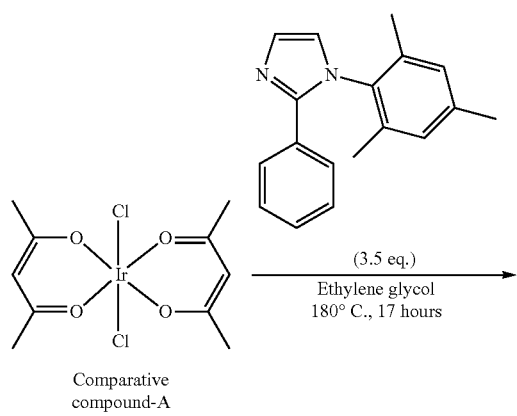

Comparative compound-A (D-3)

[Chemical Formula 15]

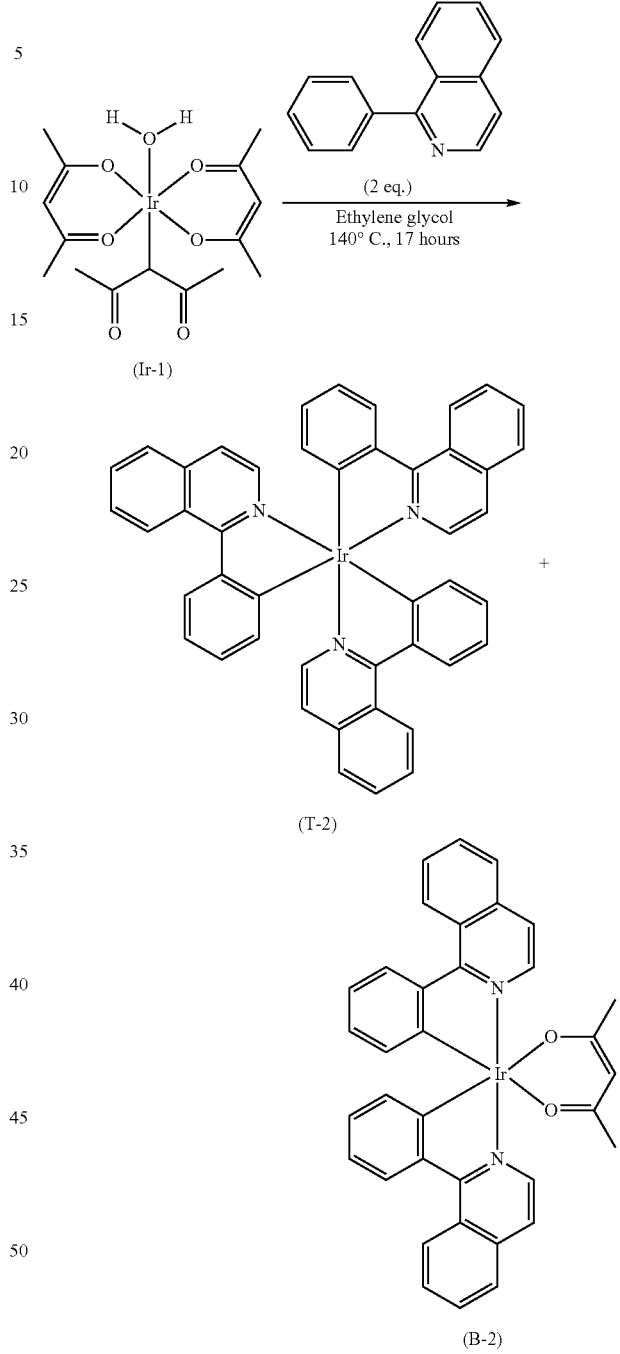

<Comparative Example 4>: Synthesis of Cyclometalated Iridium Complexes (T-2) and (B-2)

104.2 mg (0.2 mmol) of the iridium compound (Ir-1), 82.1 mg (0.4 mmol) of 1-phenylisoquinoline and 1.7 ml of ethylene glycol were mixed, and the mixture was heated and reacted in an argon atmosphere at 140° C. for 17 hours. After completion of the reaction, the reaction solution was cooled to room temperature, and extracted with dichloromethane, and the organic layer was recovered. The obtained red solid was recrystallized with dichloromethane and methanol.

The result of analysis of $^1$H-NMR showed that the product was a mixture of a cyclometalated iridium complex (T-2) and a cyclometalated iridium complex (B-2). The yields of (T-2) and (B-2) were 11% and 66%, respectively. The reaction formula here is shown below.

<Comparative Example 5>: Synthesis of Cyclometalated Iridium Complexes (T-4) and (B-4)

104.2 mg (0.2 mmol) of the iridium compound (Ir-1), 293.2 mg (1.2 mmol) of 2-methyldibenzo[f,h]quinoxaline and 1.7 ml of ethylene glycol were mixed, and the mixture was heated and reacted in an argon atmosphere at 180° C. for 17 hours. After completion of the reaction, the reaction solution was cooled to room temperature, and a red solid precipitated by addition of methanol to the reaction solution was recovered.

The result of analysis of ¹H-NMR showed that the product was a mixture of a cyclometalated iridium complex (T-4) and a cyclometalated iridium complex (B-4). The yields of (T-4) and (B-4) were 54% and 7%, respectively. The reaction formula here is shown below.

[Chemical Formula 16]

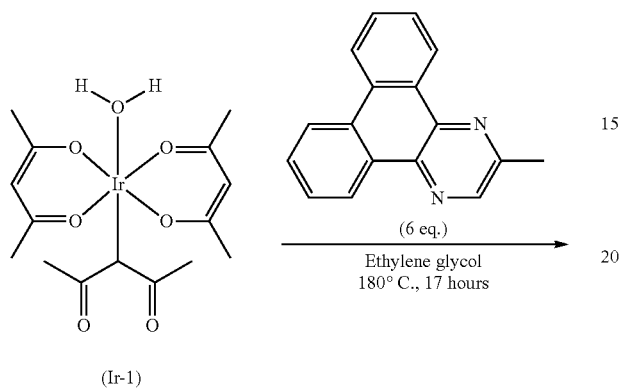

(Ir-1)

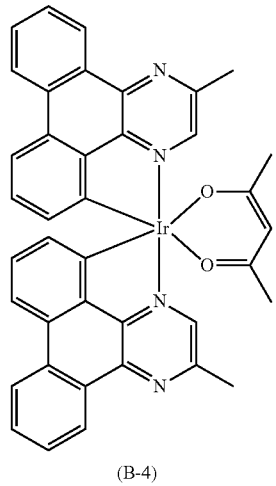

(B-4)

The results of the synthesis tests of cyclometalated iridium complexes in Examples 1 to 5 and Comparative Examples 1 to 3 are collectively shown in Table 1 below.

TABLE 1

| | Ir compound | Ligand/added amount | Yield | |
|---|---|---|---|---|
| Example 1 | Ir-1 | 2-phenylpyridine/3.5 (e.q) | T-1: 62% | |
| Comparative Example 1 | Comparative compound-A | | T-1: 22% | D-1: 73% |
| Example 2 | Ir-1 | 1-phenylisoquinoline/6.0 (e.q) | T-2: 60% | |
| Comparative Example 2 | Comparative compound-A | | T-2: 24% | D-2: 66% |
| Example 3 | Ir-1 | 1-mesityl-2-phenyl-1H-imidazole/3.5 (e.q) | T-3: 54% | |
| Comparative Example 3 | Comparative compound-A | | — | D-3: 23% |
| Example 4 | Ir-1 | 1-phenylisoquinoline/2.0 (e.q) | T-2: 11% B-2: 66% | |
| Example 5 | Ir-1 | 2-methyldibenzo[f,h]quinoxaline/6.0 (e.q) | T-4: 54% B-4: 7% | |

T: Cyclometalated iridium complex (m = 3)
B: Cyclometalated iridium complex (m = 2)
D: Halogen-crosslinked iridium dimer -continued

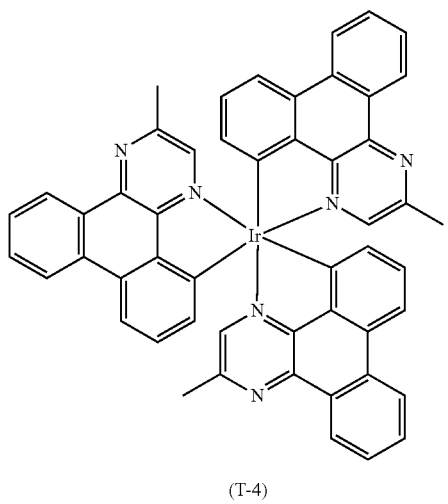

(T-4)

+

First, examination of the results in Examples 1 to 3 showed that by use of the iridium compound (Ir-1) as a raw material, a desired cyclometalated iridium complex alone was obtained. On the other hand, it was revealed that in Comparative Examples 1 to 3 using the conventional comparative compound-A as a raw material, an undesired halogen-crosslinked iridium dimer was obtained as a main product, and the yield and the purity of a desired cyclometalated iridium complex were considerably reduced (Comparative Examples 1 and 2), or the cyclometalated iridium complex was not generated at all (Comparative Example 3).

In addition, it was confirmed that as in Examples 4 and 5, it was possible to produce a cyclometalated iridium complex in which the coordination number (m) of the aromatic heterocyclic bidentate ligand was 2. In Examples 2 and 4, the same aromatic heterocyclic bidentate ligand (1-phenylisoquinoline) was reacted, but cyclometalated iridium complexes different in coordination number (m) of the aromatic heterocyclic bidentate ligand can be produced by adjustment of the added amount of the aromatic heterocyclic bidentate ligand. It is indicated that the present invention is useful over a wide range.

Further, it is apparent from the reaction conditions in examples in the present invention, a cyclometalated iridium complex can be produced without use of an excessive amount of an aromatic heterocyclic bidentate ligand. In addition, a cyclometalated iridium complex with a high purity is obtained, and therefore it may be possible to considerably reduce costs associated with purification and production.

INDUSTRIAL APPLICABILITY

The present invention allows a cyclometalated iridium complex which is a phosphorescent material for organic EL devices etc. to be produced with a favorable yield and a favorable purity. Further, an organic EL device or the like with high efficiency can be produced by use of a cyclometalated iridium complex produced by the method of the present invention. The present invention is extremely useful as a method for producing a cyclometalated iridium complex that is used as a phosphorescent material to be used for organic electroluminescent (EL) devices, organic electrochemiluminescent (ECL) devices, luminescent sensors, photosensitizing pigments, photocatalysts, luminescent probes, various light sources, and the like.

The invention claimed is:

1. A method for producing a cyclometalated iridium complex represented by the following Formula (3), the method comprising producing a cyclometalated iridium complex by reacting a cyclometalated iridium complex raw material including an organoiridium material represented by the following Formula (1) with an aromatic heterocyclic bidentate ligand capable of forming an iridium-carbon bond and represented by the following Formula (2) and an iridium-nitrogen bond, wherein the aromatic heterocyclic bidentate ligand represented by the Formula (2) is reacted with 1.5 times or more and less than 3 times the molar amount of the iridium compound represented by the Formula (1);

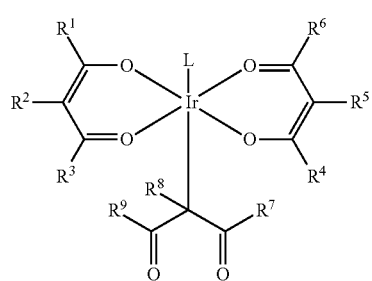

Formula (1)

(in Formula (1), Ir represents an iridium atom, and O represents an oxygen atom; L represents a ligand capable of forming an iridium-oxygen bond; $R^1$, $R^3$, $R^4$, $R^6$, $R^7$ and $R^9$ each independently represent an alkyl group; $R^2$, $R^5$ and $R^8$ each independently represent a hydrogen atom or an alkyl group; and some or all of hydrogen atoms of the alkyl group may be substituted with halogen atoms),

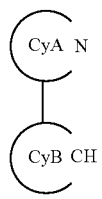

Formula (2)

(in Formula (2), N represents a nitrogen atom, C represents a carbon atom, H represents a hydrogen atom, CyA represents a five-membered or six-membered cyclic group containing nitrogen atoms, CyB represents a five-membered or six-membered cyclic group containing carbon atoms, and CyA and CyB may be linked together to form a ring structure), and

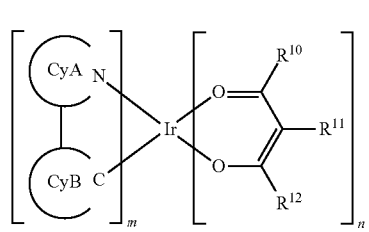

Formula (3)

(in Formula (3), Ir represents an iridium atom, N represents a nitrogen atom, C represents a carbon atom, CyA represents a five-membered or six-membered cyclic group containing nitrogen atoms, and is linked to iridium via the nitrogen atoms, and CyB represents a five-membered or six-membered cyclic group containing carbon atoms, and is linked to iridium via the carbon atoms; CyA and CyB may be linked together to further form a ring structure; $R^{10}$ and $R^{12}$ each independently represent an alkyl group, $R^{11}$s each independently represent a hydrogen atom or an alkyl group, and some or all of hydrogen atoms of the alkyl group may be substituted with halogen atoms; m is 2, and n is 1).

2. The method for producing a cyclometalated iridium complex according to claim 1, wherein $R^2$, $R^5$, $R^8$ and $R^{11}$ each independently represent a hydrogen atom.

3. The method for producing a cyclometalated iridium complex according to claim 1, wherein the ligand L is $H_2O$.

4. The method for producing according to claim 2, wherein CyA is any one of a pyridine ring, a pyrimidine ring, a pyrazine ring, a pyridazine ring, a quinoline ring, an isoquinoline ring, a quinoxaline ring, a cinnoline ring, a phthalazine ring, a quinazoline ring, a naphthyridine ring, an imidazole ring, a pyrazole ring, a triazole ring, a tetrazole ring, an oxazole ring, an oxadiazole ring, a thiazole ring, and a thiadiazole ring, and CyB is any one of a benzene ring, a naphthalene ring, an anthracene ring, a carbazole ring, a fluorene ring, a furan ring, a thiophene ring, a pyridine ring, a pyrimidine ring, a pyrazine ring, a pyridazine ring, a quinoline ring, an isoquinoline ring, a quinoxaline ring, a cinnoline ring, a phthalazine ring, a quinazoline ring, a naphthyridine ring, an imidazole ring, a pyrazole ring, a triazole ring, a tetrazole ring, an oxazole ring, an oxadiazole ring, a thiazole ring, and a thiadiazole ring.

5. The method for producing a cyclometalated iridium complex according to claim 2, wherein the ligand L is $H_2O$.

6. The method for producing according to claim 3, wherein CyA is any one of a pyridine ring, a pyrimidine ring, a pyrazine ring, a pyridazine ring, a quinoline ring, an isoquinoline ring, a quinoxaline ring, a cinnoline ring, a phthalazine ring, a quinazoline ring, a naphthyridine ring, an imidazole ring, a pyrazole ring, a triazole ring, a tetrazole ring, an oxazole ring, an oxadiazole ring, a thiazole ring, and a thiadiazole ring, and CyB is any one of a benzene ring, a naphthalene ring, an anthracene ring, a carbazole ring, a fluorene ring, a furan ring, a thiophene ring, a pyridine ring, a pyrimidine ring, a pyrazine ring, a pyridazine ring, a quinoline ring, an isoquinoline ring, a quinoxaline ring, a cinnoline ring, a phthalazine ring, a quinazoline ring, a naphthyridine ring, an imidazole ring, a pyrazole ring, a triazole ring, a tetrazole ring, an oxazole ring, an oxadiazole ring, a thiazole ring, and a thiadiazole ring.

\* \* \* \* \*